United States Patent
Roh et al.

(10) Patent No.: US 8,777,861 B2
(45) Date of Patent: Jul. 15, 2014

(54) THREE-DIMENSIONAL ULTRASONIC SCANNER

(75) Inventors: Yongrae Roh, Daegu (KR); Susung Lee, Yongin-Si (KR); Hyungkeun Lee, Daegu (KR); Jeongdong Woo, Daegu (KR); Wonseok Lee, Daegu (KR); Hoyoung Lee, Seoul (KR); Eunhee Shin, Daegu (KR)

(73) Assignees: Alpinion Medical Systems Co., Ltd. (KR); Kyungpook National University Industry-Academic Cooperation Foundation (KR)

( * ) Notice: Subject to any disclaimer, the term of this patent is extended or adjusted under 35 U.S.C. 154(b) by 0 days.

(21) Appl. No.: 13/386,131

(22) PCT Filed: Jul. 23, 2010

(86) PCT No.: PCT/KR2010/004857
§ 371 (c)(1),
(2), (4) Date: Jan. 20, 2012

(87) PCT Pub. No.: WO2011/010896
PCT Pub. Date: Jan. 27, 2011

(65) Prior Publication Data
US 2012/0123269 A1    May 17, 2012

(30) Foreign Application Priority Data
Jul. 24, 2009   (KR) .................. 10-2009-0067761

(51) Int. Cl.
*A61B 8/14*   (2006.01)
(52) U.S. Cl.
USPC ......................... 600/459; 600/437

(58) Field of Classification Search
USPC .................................. 600/437–469
See application file for complete search history.

(56) References Cited

U.S. PATENT DOCUMENTS 4,807,634 A   2/1989  Enjoji et al.
4,841,979 A * 6/1989  Dow et al. .................... 600/446
(Continued)

FOREIGN PATENT DOCUMENTS

GB          2067759 A    7/1981
JP      2007021170 A    2/2007
(Continued)

OTHER PUBLICATIONS

International Search Report (in Korean with English Translation) for PCT/KR2010/004857, mailed Apr. 4, 2011; ISA/KR.

*Primary Examiner* — Sanjay Cattungal
(74) *Attorney, Agent, or Firm* — Harness, Dickey & Pierce, P.L.C.

(57) ABSTRACT

The present disclosure provides a precise performance three-dimensional ultrasound scanner that is lightweight for an easy hold by suggesting a novel constitution of a swing mechanism wherein an arrangement of the drive motor perpendicular to the swing axis requires a smaller capacity motor and eliminating a backlash. The swing mechanism includes: an arm holder connected to a rotational axis of the motor; an arm connected to the arm holder so that the arm swings within a certain angular range; a link, attached to the arm, for moving in unison with the arm; a shaft, connected to the link, for transmitting a rotary power of the arm to the transducer unit. The swing mechanism can be operated using the smaller capacity motor and eliminates the need for a pulley, gear or belt eliminating backlashes to promote implementation of lightweight precision three-dimensional ultrasound scanners.

17 Claims, 4 Drawing Sheets

(56) References Cited

U.S. PATENT DOCUMENTS

| | | | |
|---|---|---|---|
| 4,895,158 A * | 1/1990 | Kawabuchi et al. | 600/463 |
| 5,048,529 A * | 9/1991 | Blumenthal | 600/446 |
| 5,090,414 A * | 2/1992 | Takano | 600/461 |
| 5,255,684 A * | 10/1993 | Rello | 600/463 |
| 5,351,692 A * | 10/1994 | Dow et al. | 600/463 |
| 5,450,851 A * | 9/1995 | Hancock | 600/462 |
| 5,469,852 A * | 11/1995 | Nakamura et al. | 600/463 |
| 5,479,929 A * | 1/1996 | Cooper et al. | 600/459 |
| 5,494,040 A * | 2/1996 | Nakao et al. | 600/463 |
| 5,662,116 A * | 9/1997 | Kondo et al. | 600/462 |
| 5,833,616 A * | 11/1998 | Gruner et al. | 600/462 |
| 6,709,397 B2 * | 3/2004 | Taylor | 600/459 |
| 6,840,938 B1 * | 1/2005 | Morley et al. | 606/51 |
| 7,635,335 B2 | 12/2009 | Hwang | |
| 7,819,809 B2 | 10/2010 | Kim | |
| 8,083,681 B2 * | 12/2011 | Kadokura | 600/459 |
| 2005/0288587 A1 | 12/2005 | Roh et al. | |
| 2006/0173330 A1 | 8/2006 | Kim | |
| 2007/0016060 A1 | 1/2007 | Hwang | |
| 2008/0287801 A1 | 11/2008 | Magnin et al. | |
| 2010/0156404 A1 | 6/2010 | Han et al. | |

FOREIGN PATENT DOCUMENTS

| | | | |
|---|---|---|---|
| JP | 2008278932 A | 11/2008 | |
| KR | 100562886 B1 | 3/2006 | |
| KR | 1020060076026 A | 7/2006 | |

* cited by examiner

THREE-DIMENSIONAL ULTRASONIC SCANNER

TECHNICAL FIELD

The present disclosure relates to a three-dimensional ultrasound scanner. More particularly, the present invention relates to a three-dimensional ultrasound scanner which provides a swing mechanism for making the scanner easy to hold and lightweight to maneuver in order to enhance the user convenience.

BACKGROUND ART

The statements in this section merely provide background information related to the present disclosure and may not constitute the prior art.

In the medical field, ultrasound diagnosis technology is widely known. Ultrasound diagnosis equipment is comprised of a main body for ultrasound diagnosis and an ultrasound scanner. The ultrasound scanner includes an array transducer consisting of a number of transducers for transmitting and receiving ultrasound waves. When the ultrasound scanner is positioned on the skin of body, the ultrasound waves transmitted from the array transducer is reflected back after hitting the object for diagnosis. The ultrasound diagnosis equipment processes and analyzes the reflected signals to provide a visual representation of cross-sectional images of the interior of the body through a monitor.

If the array transducer is fixedly installed in the ultrasound scanner, it is very difficult to synthesize a three-dimensional image. A user may deliberately tilt or move the ultrasound scanner to obtain a three-dimensional image but an observation of the object for diagnosis at an optimal angle and location can hardly be achieved and a distortion will occur during data acquisition.

FIG. 1 illustrates an internal constitution of conventional three-dimensional ultrasound scanner.

As illustrated, 3-D ultrasound scanner 10 is enclosed by a scanner case 12 which houses an array transducer 14 positioned in reciprocating movement due to a swing mechanism 16. Scanner case 12 is internally divided by a base 18 into two spaces. Swing mechanism 16 is positioned in a top space above base 18, and array transducer 14 is positioned in a bottom space below base 18.

Swing mechanism 16 is comprised of a motor 20 which rest on base 18, gears 22, a shaft 24, and an arm 26. Array transducer 14 is constructed to hang on swing mechanism 16 through arm 26. In this construction, when motor 20 starts, gears 22, shaft 24, and arm 26 make sequential movements for impelling array transducer 14 to carry out a swing motion about the axis of shaft 24. With repetitive swing motions of array transducer 14, there are sequentially repeated acquisitions of scanned surfaces within the range of the swing, whereby a three-dimensional ultrasound image may be generated.

DISCLOSURE

Technical Problem

However, the conventional 3-D ultrasound scanner has a problem of causing inconvenience to the user with holding the scanner by hand because the placement of the motor alongside the swing axis inflates the scanner handle portion.

In addition, since conventional 3-D ultrasound scanners utilize multiple pulleys, belts, or gears which increases the reduction gear ratio requiring a high-speed and hence a high capacity motor, they end up to become problematic heavyweight products.

Such heavy and inconvenient scanner construction causes a wrist pain for frequent scanner users.

Moreover, employment of pulleys, belts, or gears involves the difficulty of making alignments to a level of required precision in manufacturing the scanner and causes backlash between the components leading to imprecise images at the scene of the three-dimensional ultrasound diagnosis and even results in scanner malfunctions.

Technical Solution

In view of the foregoing problems, the present disclosure provides a lightweight and comfortable three-dimensional ultrasound scanner which is not hard on the users' wrists in carrying out the ultrasound diagnosis.

In addition, the present disclosure provides a three-dimensional ultrasound scanner that eliminates a backlash from a swing mechanism to thereby offer a high precision.

For this purpose, the three-dimensional ultrasound scanner according to an aspect of the present disclosure includes: a scanner case; a transducer unit positioned on an interior floor of the scanner case; a motor positioned perpendicular to a swing axis of the transducer unit; and a swing mechanism for transmitting a rotary power of the motor to the transducer unit to reciprocate the transducer unit.

Additionally, the three-dimensional ultrasound scanner according to another aspect of the present disclosure includes: a scanner case including a handle and a scanning body; a transducer unit positioned on an interior floor of the scanner body; a motor, inserted in the handle, having a rotational axis perpendicular to a swing axis of the transducer unit; a first power transmitter following a rotary operation of the motor to swing about an axis of rotation within a certain angular range; and a second power transmitter for transmitting a rotary power of the first power transmitter to the transducer unit to reciprocate the transducer unit.

Furthermore, the three-dimensional ultrasound scanner according to yet another aspect of the present disclosure includes: a scanner case; a transducer unit positioned on an interior floor of the scanner case; a motor for generating a rotary power for causing a reciprocating movement of the transducer unit; an arm holder connected to a rotational axis of the motor; an arm connected to the arm holder to rotate about the rotational axis of the motor within a certain angular range; a link, attached to the arm, for moving in unison with the arm; and a shaft, connected to the link, for transmitting a rotary power of the arm to the transducer unit.

Advantageous Effects

As mentioned above, the arrangement of the drive motor for the swing mechanism as perpendicular to the swing axis of the transducer unit gives more flexibility in the design of the handle of the three-dimensional ultrasound scanner for a user to hold.

In addition, the simplified swing mechanism capable of employing a smaller capacity motor facilitates the implementation of a lighter three-dimensional ultrasound scanner.

Further, eliminating the need for pulleys, belts or gears precludes an alignment issue in manufacturing the scanners, while backlashes due to worn out components are virtually zero, which promotes implementation of precision three-dimensional ultrasound scanners.

MODE FOR INVENTION

Figure 1:
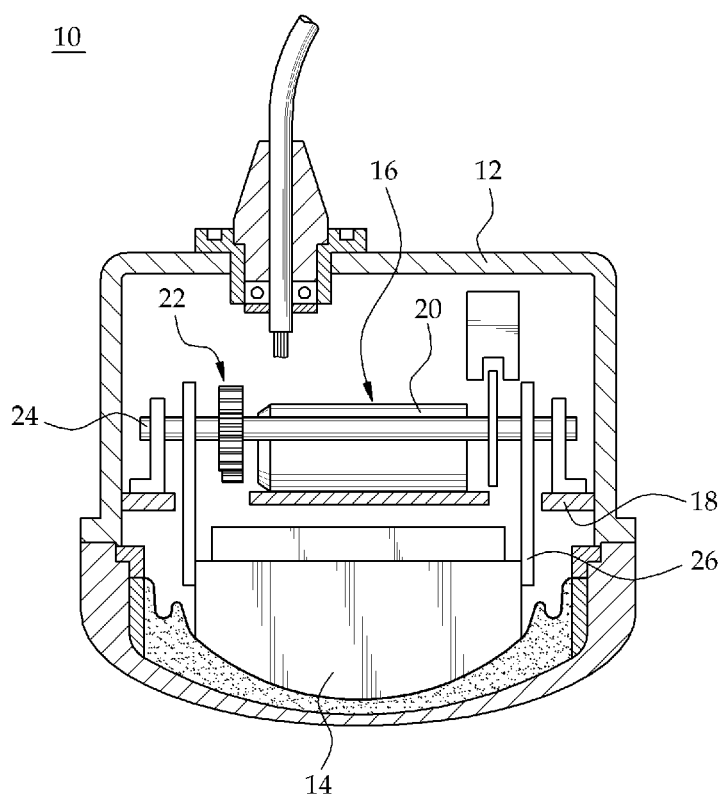
FIG. 1 is a diagram illustrating a conventional three-dimensional ultrasound scanner.

First of all, the present disclosure provides a precise performance three-dimensional ultrasound scanner that is agile for a hand to easily hold by suggesting a novel construction of a swing mechanism wherein an arrangement of the drive motor perpendicular to the swing axis requires a small capacity motor, eliminating a backlash from occurring.

In the following, as aspect of the present disclosure will be detailed referring to the drawings.

Figure 2:
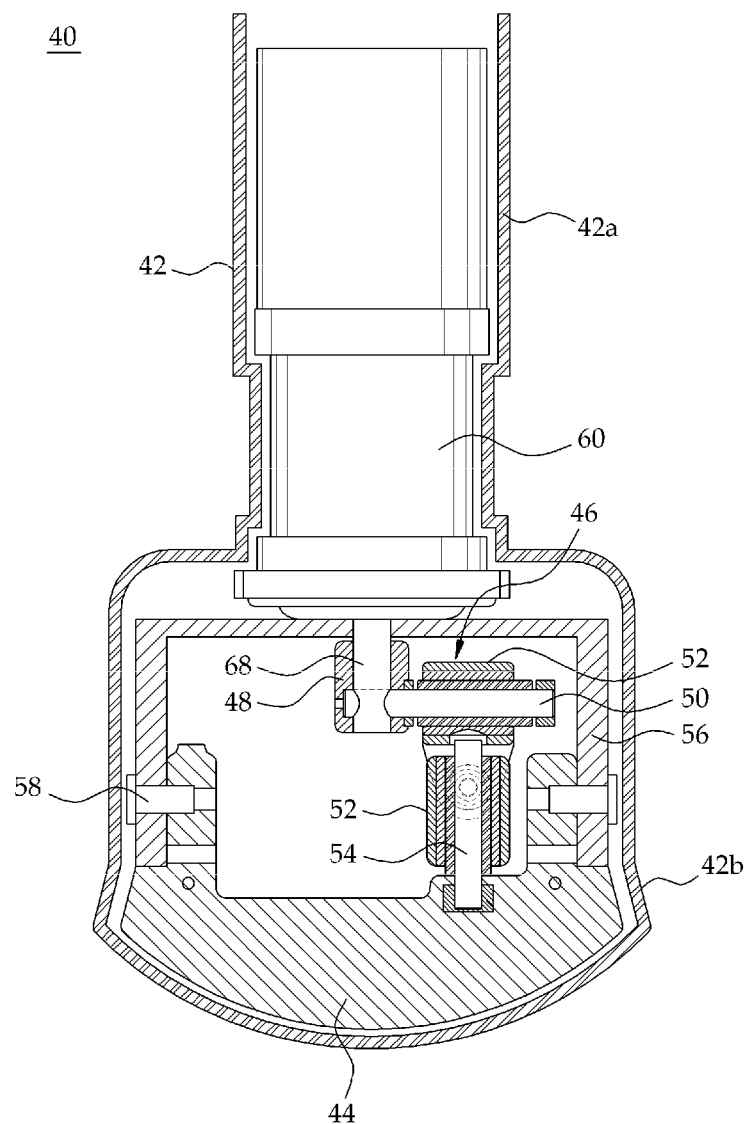
FIG. 2 is a cross sectional view of a three-dimensional ultrasound scanner according to the present disclosure.

FIG. 2 is a cross sectional view of a three-dimensional ultrasound scanner according to the present disclosure.

As shown in FIG. 2, a three-dimensional ultrasound scanner 40 is enclosed by a scanner case 42 which houses a transducer unit 44 having a number of transducers for transmitting and receiving ultrasound waves, a swing mechanism 46 for reciprocating transducer unit 44, a motor 60 for generating a rotary power for operating swing mechanism 46.

A novel arrangement of swing mechanism 46 and motor 60 shapes scanner case 42 to have a handle 42a and a scanning body 42b. Motor 60 is positioned in handle 42a of scanner 40 and transducer unit 44 is positioned on an internal floor of scanning body 42b.

Although not shown, transducer unit 44 is comprised of a number of transducer elements arranged over a convex surface, an acoustic lens for converging ultrasound waves transmitted from a number of transducer elements, matching layer for providing an impedance matching between the transducer elements and the lens, and backing layer for absorbing unnecessary portion of ultrasound waves. Transducer unit 44 reciprocates with the assistance of swing mechanism 46, sequentially repeating acquisitions of scanned surfaces within the range of the reciprocating motion.

Figure 3:
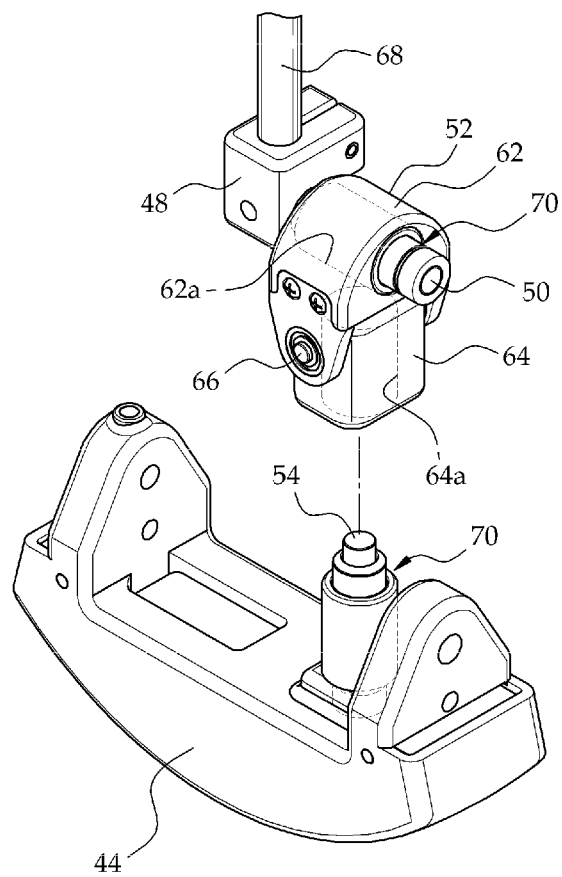
FIG. 3 is a perspective view of a swing mechanism according to the present disclosure.

Swing mechanism 46 includes an arm holder 48, an arm 50, and a shaft 54. Referring to FIGS. 2 and 3, the construction of swing mechanism 46 will be described in detail. Arm holder 48 is connected to an axis 68 of rotation of motor 60 to transmit the rotary power of motor 60 to arm 50. Arm 50 is co-rotationally connected to arm holder 48 so that the arm 50 rotates about axis 68 of rotation of motor 60 within a certain angular range. A link 52 is connected to arm 50 to move therewith. The structure of link 52 will be described with reference to FIG. 4. Shaft 54 is connected to link 52 for transmitting the rotary power of arm 50 to transducer unit 44.

Inside scanner case 42 is a frame 56 installed to place motor 60 in its upper space and transducer unit 44 in its lower space. Transducer unit 44 is constructed to hang on a swing axis 58 installed on opposite ends of frame 58 so that transducer unit 44 swings about swing axis 58. Motor 60 is seated on top of frame 56 so that axis 68 of rotation of motor 60 may be perpendicular to swing axis 58.

Upon receiving power from a power source, motor 60 rotates which also turns arm holder 48 together with its coupled axis 68. Motor 60 repeats forward and reverse rotations at a predetermined angular velocity within a certain angular range. Accordingly, arm 50 connected to arm holder 48 swings repeatedly about axis 68 within the certain angular range.

Rotational reciprocation of arm 50 is transmitted via link 52 to shaft 54 mounted on top of transducer unit 44. Link 52 connects arm 50 and shaft 54 to effectively transmit the rotary power of arm 50 to transducer unit 44. When the reciprocating rotational movement of arm 50 is transmitted through link 52 to shaft 54, shaft 54 follows arm 50 in its rotational directions to thrust transducer unit 44 sideways in reciprocation.

Figure 4:
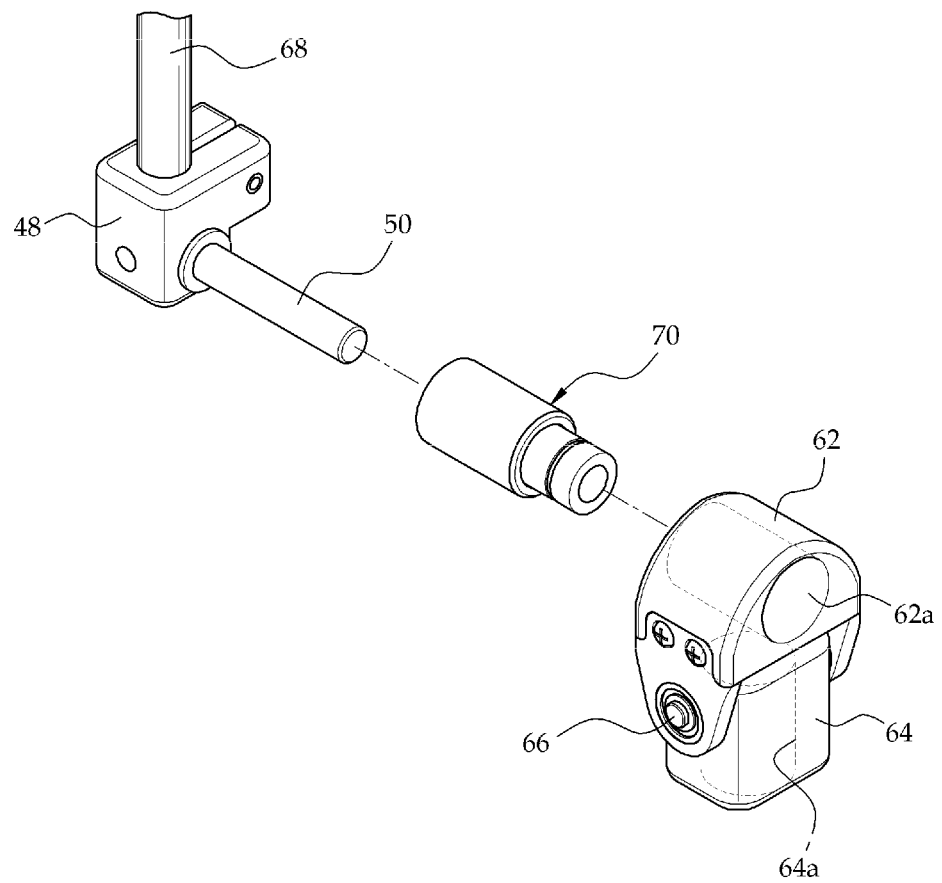
FIG. 4 is a perspective view of a link according to the present disclosure.

Referring to FIG. 4, link 52 is comprised of two members. Specifically, link 52 is made of a first link member 62 having an opening 62a for arm 50 and a second link member 64 having a bore 64a for accepting shaft 54. First link member 62 and second link member 64 are connected by a link coupler 66, and they are preferably interconnected through a ball bearing. Articulated by the ball bearing, link 52 is adapted to compensate for the changes in angle between arm 50 and shaft 54.

A ball bushing system 70 is applied to opening 62a of first link member 62 for receiving arm 50 as well as to bore 64a of second link member 64 for receiving shaft 54. Ball bushing system 70 mainly plays the role of reducing frictional forces between arm 50, shaft 54, and link 52 during the repetitive rotational reciprocation.

A person skilled in the art could improve or diversify the technical idea of the present disclosure into different forms. Therefore, present disclosure should not be understood restrictedly by the very aspect stated but the scope of right of the present disclosure should be strictly understood as what is claimed below and its equivalent idea.

Cross-Reference to Related Application

If applicable, this application claims priority under 35 U.S.C §119(a) on Patent Application No. 10-2009-0067761 filed in Korea on Jul. 24, 2009, the entire content of which is hereby incorporated by reference. In addition, this non-provisional application claims priority in countries, other than the U.S., with the same reason based on the Korean Patent Application, the entire content of which is hereby incorporated by reference.

The invention claimed is:

1. A three-dimensional ultrasound scanner without internal pulleys comprising:
   a transducer unit connected to a swing axis;
   a motor generating rotary power; and
   a swing mechanism configured to transmit the rotary power of the motor to the transducer unit to swing the transducer unit about the swing axis;
   wherein the swing mechanism comprises;
      an arm holder connected to a rotational axis of the motor;
      an arm connected to the arm holder, and configured to swing within a certain angular range about the rotational axis depending on rotation of the motor;
      a link attached to the arm for moving in unison with the arm; and
      a shaft connected to the link and the transducer unit, and configured to thrust the transducer unit sideways, depending on the swing movement of the arm delivered to the shaft via the link, to thereby swing the transducer unit about the swing axis; and
   wherein the link comprises:
      a first link member; and
      a second link member connected via a link coupler to the first link member.

2. The three-dimensional ultrasound scanner of claim 1, wherein the rotational axis of the motor is perpendicular to the swing axis of the transducer unit.

3. The three-dimensional ultrasound scanner of claim 1, wherein the first link member comprises a first opening for receiving the arm and the second link member comprises a second opening for receiving the shaft.

4. The three-dimensional ultrasound scanner of claim 3 wherein a first linear guide is arranged in the first opening to allow the first link member to move along the arm depending on the rotation of the motor, and a second linear guide is arranged in the second opening to allow the second link member to move along the shaft depending on the rotation of the motor.

5. The three-dimensional ultrasound scanner of claim 4 wherein said each linear guide is a ball bush.

6. The three-dimensional ultrasound scanner of claim 1, wherein the link coupler is a ball bearing.

7. The three-dimensional ultrasound scanner of claim 1, wherein the arm is extended from the arm holder in a radius direction of the rotational axis of the motor.

8. The three-dimensional ultrasound scanner of claim 7, wherein the shaft is extended from the link in a direction different from the direction in which the arm is extended from the arm holder.

9. The three-dimensional ultrasound scanner of claim 1, wherein a swing plane of the transducer is different from a swing plane of the arm.

10. The three-dimensional ultrasound scanner of claim 9, wherein the swing plane of the transducer is perpendicular to the swing plane of the arm.

11. A method for rotating a transducer unit by actuation of a motor of an ultrasound scanner and without using pulleys, the method comprising:
    swinging an arm within a certain angular range based on rotation of the motor, wherein the arm is connected to a rotational axis of the motor and is extended from the rotational axis in a radius direction;
    delivering the swing movement of the arm to a shaft via a link, wherein the link connects between the arm and the shaft, and the shaft is extended from the link in a direction different from the direction in which the arm is extended from the rotational axis;
    swinging the shaft depending on the swing movement of the arm delivered to the shaft via the link; and
    thrusting the transducer unit sideways by the swing movement of the shaft to thereby swing the transducer unit about a swing axis;
    wherein the link comprises a first link member configured to accept the arm and a second link member configured to accept the shaft and connected to the first link member via a link coupler.

12. The method of claim 11, wherein delivering the swing movement of the arm comprises sliding the first link member along the arm and sliding the second link member along the shaft, depending on the swing movement of the arm.

13. A three-dimensional ultrasound scanner without internal pulleys comprising:
    a motor generating rotary power output, the motor including a rotational axis;
    an arm radially extending from the rotational axis in a first direction;
    a link member coupled to the arm and moved by the arm;
    a shaft coupled to the link member, the shaft extending in a second direction that is different from the first direction in which the arm extends; and
    a transducer unit coupled to the shaft and movable about a swing axis in response to movement of the arm;
    wherein the link member comprises a first portion defining a first opening and a second portion defining a second opening, and a link coupler connects the first portion and the second portion together.

14. The three-dimensional ultrasound scanner of claim 13, wherein the arm extends perpendicular to the shaft.

15. The three-dimensional ultrasound scanner of claim 13, wherein the rotational axis of the motor is perpendicular to the swing axis of the transducer unit.

16. The three-dimensional ultrasound scanner of claim 13, wherein the second opening extends generally perpendicular to the first opening, the arm is received within the first opening, and the shaft is received within the second opening.

17. The three-dimensional ultrasound scanner of claim 13, wherein the link coupler is a ball bearing.

* * * * *